United States Patent [19]

Stanley, Jr., deceased

[11] Patent Number: 5,652,292
[45] Date of Patent: Jul. 29, 1997

[54] SUSPENSION POLYMERIZED AQUEOUS ABSORBENT POLYMER PARTICLES

[75] Inventor: Frederick W. Stanley, Jr., deceased, late of Midland, Mich., by Caroline Stanley, legal representative

[73] Assignee: The Dow Chemical Company, Midland, Mich.

[21] Appl. No.: 464,776

[22] PCT Filed: Feb. 26, 1993

[86] PCT No.: PCT/US93/02144

§ 371 Date: Jun. 22, 1995

§ 102(e) Date: Jun. 22, 1995

[87] PCT Pub. No.: WO94/19377

PCT Pub. Date: Sep. 1, 1994

[51] Int. Cl.$^6$ .................. C08F 220/06; C08F 265/02
[52] U.S. Cl. .................. 524/458; 523/200; 523/205; 523/220; 523/223; 524/534; 524/801; 524/823; 525/252; 526/200; 526/207
[58] Field of Search .................. 526/207, 200; 523/220, 223, 202, 205; 524/534, 458, 801, 823; 525/252

[56] References Cited

U.S. PATENT DOCUMENTS

| | | | |
|---|---|---|---|
| 4,134,815 | 1/1979 | Jackson et al. | 526/207 |
| 4,446,261 | 5/1984 | Yamasaki et al. | 524/40 |
| 4,666,975 | 5/1987 | Yamasaki et al. | 524/733 |
| 4,683,274 | 7/1987 | Nakamura et al. | 526/216 |
| 4,708,997 | 11/1987 | Stanley et al. | 526/207 |
| 4,833,222 | 5/1989 | Siddall et al. | 526/200 |
| 5,374,684 | 12/1994 | Tai | 525/254 |

FOREIGN PATENT DOCUMENTS

| | | | |
|---|---|---|---|
| 3617311 | 2/1987 | Germany | C08F 2/18 |
| 3741158 | 6/1989 | Germany. | |
| 2119384 | 11/1983 | United Kingdom. | |

*Primary Examiner*—Andrew E. C. Merriam

[57] ABSTRACT

A process for making clusters of individual polymer beads bonded together to minimize attritition in use or processing but characterized by an open structure for fast absorption of aqueous solutions comprises suspending a monomer mixture in a continuous phase at high shear agitation such that fine droplets of monomer are formed in an inert organic phase. A suspending agent which prevents the clusters from coalescing is provided. A first polyethylenically unsaturated crosslinking monomer, having substantial solubility in the aqueous phase, and an organic phase soluble initiator system are provided such that polymerization at the surface of the polymer particles occurs to form the porous clusters of the invention, A second substantially oil soluble crosslinker is optionally provided to further crosslink the clusters such that they do not coalesce.

19 Claims, 1 Drawing Sheet

SUSPENSION POLYMERIZED AQUEOUS ABSORBENT POLYMER PARTICLES

The present invention relates to a process for preparing a suspension polymerized aqueous fluid absorbent polymer material.

Many water insoluble gel-forming polymers are known for their usefulness as absorbents because of their ability to imbibe and bind or immobilize aqueous fluids. These polymeric materials find employment in industry for various dewatering and fluid immobilization uses, such as water retaining agents in agricultural/horticultural fields, dehydration of oil, and like purposes.

In recent years, absorbent polymers having large capacities for absorbing aqueous fluids have been developed and have found use in personal care products for absorbing aqueous biological fluids. In a typical personal care product, such as a diaper, the aqueous fluid absorbent polymer, in a powder form is mixed with cellulosic fibers that help initially absorb and distribute the fluid load. The polymeric materials of interest in such products are based upon a variety of polymers, including those derived from water soluble ethylenically unsaturated monomers or graft polymers in which unsaturated monomers are graft polymerized onto a polysaccharide (such as starch or cellulose) or other polymeric backbones.

A preferred absorbent material is derived from a water insoluble gel that is formed by copolymerizing an ethylenically unsaturated carboxylic acid with a multifunctional crosslinking monomer. The acid monomer is often substantially neutralized with an alkali metal hydroxide before polymerization. After polymerization, the resulting polymer is dried and pulverized into a powder form before use, for example, in a personal care product. A preferred polymer gel is a copolymer of acrylic acid/sodium acrylate and a variety of crosslinkers.

Achieving desired polymeric characteristics that provide superior performance in a personal care product has long been a challenging goal of researchers. The product must perform for the user but also must be capable of being economically and safely made. At the customer/user level, a diaper, for example, most desirably must keep the user substantially dry, even in response to repeated wettings. Thus, a key desired characteristic of an aqueous fluid absorbent polymer, at least for diaper use, is that it have high fluid capacity. In addition, a most desired characteristic of the aqueous fluid absorbent polymer is that it have a fast rate of absorption, adequate to imbibe and hold the fluid during the absorption process without leakage of fluid from the device in which it is employed. It is adequate fast rate, while maintaining all of the other desired qualities of the aqueous absorbent, that has eluded prior researchers.

It is well-known in the prior art that the rate of fluid absorbency is substantially determined by the surface area of the particles. Thus, extremely fine particles of aqueous fluid absorbent, those substantially less than 100 mesh (149 micrometers), absorb liquids at a rapid rate. However, the individual particles at the surface of a mass of such polymeric fines, when initially contacted by the fluid, rapidly swell and adhere together, in effect drastically reducing the overall rate of absorption of the polymer mass, as the fluid is "gel blocked" from access to particles of absorbent in the mass that are more remote from the surface. Lumps or "fish eyes" of material often form such that overall performance of the absorbent material is unsatisfactory.

An additional difficulty with fine materials is that such fines create dusting problems in manufacturing and forming into finished articles. At the product level it may be difficult to immobilize fine particulate materials in an article or device of interest without elaborate containment structures that increase costs and may limit the ability of the article to perform at a desired level.

A number of workers have attempted to produce a non-dusting and/or fast absorbency rate product by making somewhat larger particles that still possess useful absorbency, changing polymer particle surface characteristics or adhering fines particles together. The balancing of desirable product end-use qualities with manufacturing limitations has heretofore meant accepting one or more less desirable characteristics.

Yamasaki, et al. in U.S. Pat. No. 4,446,261 describes making a larger sized particle that avoids dusting and is said to have improved capacity and absorbency rate over the prior art. The process produces resin particles by means of a suspension polymerization process, including a water-soluble redox initiator system, that utilizes oil soluble cellulose ester or cellulose ether as a protecting colloid in order to obtain spherical particles of a size that do not cause dusting. However, while stating that the beads have a fast absorbency rate over the prior known suspension processes, only absorbency rates on the order of greater than 4 minutes for 0.5 grams of polymer to absorb 5 milliliters of saline solution, are reported.

A number of researchers have worked at improving absorption rates for water absorbent resins. Nakamura, et al. in U.S. Pat. No. 4,683,274 suggest rate improvements for -$\alpha,\beta$-unsaturated carboxylic acid-based polymers produced by inverse emulsion polymerization through inclusion of a sucrose fatty acid ester as a protective colloid agent. Water absorption rates are said to improve to about 1 minute from 15 minutes for the time required for 1 gram of resin to absorb 30 milliliters of 0.9 percent aqueous sodium chloride solution. Such improvements, while substantial, are still not sufficient for many personal care product uses.

In GB 2119384A, crosslinking the surface layer of a specific water absorbing resin having a carboxyl group with a polyhydric alcohol is said to minimize fines and gel blocking. However, while the improvement reported is significant, much higher absorption rates are still desired.

Yamasaki, et al., in U.S. Pat. No. 4,666,975 after making absorbent polymer particles, generally following U.S. '261 (cited above) which may include some initial crosslinking, conducts a post-polymerization crosslinking reaction in the presence of 10–40 weight percent water. The resulting resin particles are said to possess a crosslinking density gradient and to be of "extremely large" particle diameters, particularly greater than 100 micrometers, which particles may be in the form of flakes, spherical particles, porous particles, or botryoidal chains. The process is directed to produce particles that balance absorptive capacity with rate of absorption and gel strength. However, all the examples report water absorptive rates over a 20-minute period that do not suggest that a truly fast absorption rate material has been achieved.

In agglomeration of fines techniques, maintaining adequate absorbency generally requires that the degree of adherence or binding of the fines particles together be limited, similar to the well-known limits on crosslinking. Otherwise, fused particles are formed that may result in products that still gel-block. Limiting binding of the particles together generally produces agglomerated products that tend to be easily attrited during incorporation into finished articles, recreating the dusting problems sought to be avoided. Attrition may also occur in the finished product such that fines block distribution of fluid in an article by filling in channels and spaces in a fiber matrix.

In U.S. Pat. No. 4,708,997, Stanley, et al. teach a suspension polymerization process for making absorbent polymer particles. While directed to producing non-agglomerated particles, polymer products ranging from a large mass to large chunks to small aggregates of beads to individual spherical beads are achieved by means of varying the acrylic acid content of a polylaurylmethacrylate-acrylic acid copolymer suspending agent.

In DE 3741158A1, Chmelir, et al. agglomerate dry fines of polyacrylic acid polymer to improve absorption rates. The dry fines are mixed typically in a fluidized bed with an agglomeration aid that may be an aqueous solution or suspension of the polymer itself or any number of materials capable of adhering the particles together by various mechanisms. Exemplified is contacting less than 90 micrometer particles of a polyacrylic acid polymer with an aqueous solution of low molecular weight polyacrylic acid to yield 89–95 weight percent agglomerated particles of 90–630 micrometers in diameter.

In U.S. Pat. No. 5,374,684, filed Jan. 18, 1991, Tai agglomerates fines from a bulk polymerization process into fast-rate particles by means of a process that forms chemical bonds between individual particles. Because of the strong bonding, subsequent attrition problems, typical of the prior art, are substantially reduced. The process requires suspending the fines in an inert solvent and slowly contacting said suspension with a suspension of ethylenically unsaturated carboxylic acid monomer under polymerization conditions. Discrete clusters of particles are formed which particles are covalently bonded to each other in a random packing configuration spatially distributed to allow aqueous absorption by said particles without gel blocking of the aqueous fluid at the surface of the clusters.

The prior art processes for agglomeration may be characterized as producing agglomerates of particles that are generally either too closely agglomerated, such that a truly high surface area aqueous fluid permeable agglomerate is not formed or, too loosely bound, such that attrition and dusting occur during processing or use. Where care is taken, such as in Tai cited above, to form clusters of particles that are strongly bonded together by chemical bonds and the cluster carefully structured to permit fluid access into the interior of the cluster, the process may involve complex steps, such as requiring handling of larger amounts of inert solvent than is conventional.

It appears clear from these difficulties that new absorbent polymer agglomerates and processes for making them are needed that, in contrast to the prior art, have adequate absorbent capacity and truly high absorption rate. While large particle size absorbents and agglomerates have been made by prior workers, as noted above, they simply heretofore have not possessed adequate rates of absorbency or resistance to attrition or were not practical or economical to manufacture. Thus, it remains desirable to provide an absorbent polymer material that is an agglomerated product that does not gel block, and that has a fast rate of absorption as evidenced by a vortex rate of 1 minute or less, and is strong enough to resist attrition in manufacture and use.

The present invention provides a process for preparing a polymer material, comprising:

(a) suspending an aqueous monomer mixture comprising a water soluble ethylenically unsaturated monomer in an inert organic liquid to form a suspension characterized by a discontinuous phase of monomer droplets, said monomer mixture including a first polyethylenically unsaturated crosslinker which is characterized by a solubility in water of at least about 0.1 grams crosslinker to 100 grams water, said suspension further containing a polymerization initiator which will partition such as to provide at least about 10 ppm polymerization initiator in said inert organic liquid, said suspension further containing a suspending agent to partially stabilize said suspension;

(b) initiating the polymerization of said monomer and said crosslinker such that a crosslinking polymerization occurs at the interface between the monomer droplets and organic liquid, wherein individual particles of polymer are bonded together to form clusters.

In one particular embodiment, the process further comprises:

(c) during said polymerization, adding a second ethylenically polyunsaturated crosslinker which is characterized by a solubility in the organic liquid continuous phase greater than about 0.1 grams per 100 grams organic liquid continuous phase; and (d) further polymerizing said clusters and second crosslinker such that further polymerization occurs at the cluster/organic phase interface.

The polymer material of the invention is particularly useful as components of an article for absorbing biological fluids, such as a disposable diaper. Such an absorbent article, generally comprising the aqueous fluid absorbent polymer clusters of the invention as described above, will have a fast rate of absorption attributable at least in part to the high effective surface area of the polymer clusters.

BRIEF DESCRIPTION OF THE DRAWINGS

These and other embodiments are more fully described in the following detailed description wherein.

DETAILED DESCRIPTION OF THE INVENTION

Figure 1:
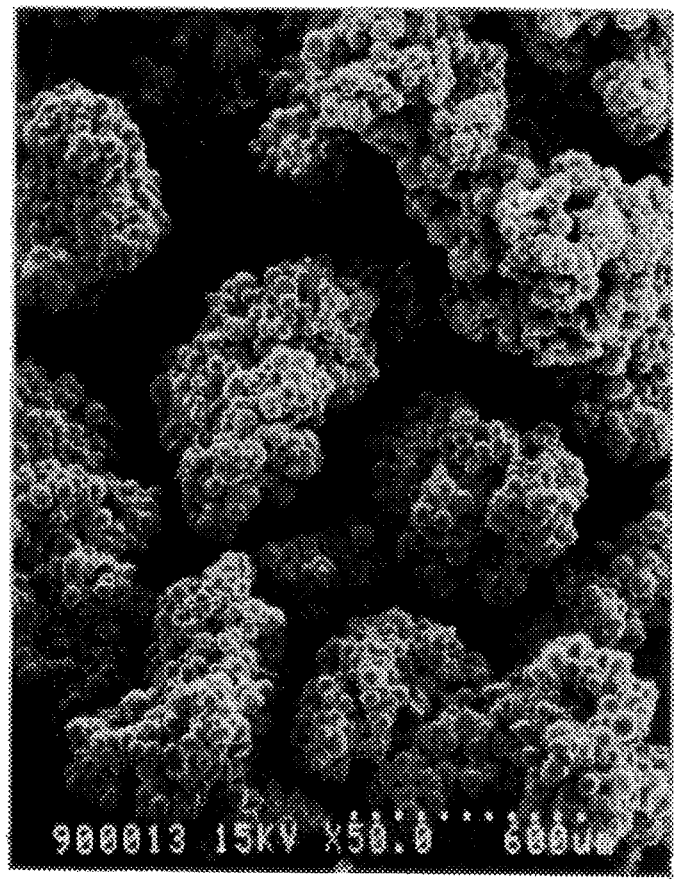
FIG. 1 is a photomicrograph, at a magnification of 50 times, of polymer clusters of the invention, prepared in accordance with Example 6 below.

In the practice of the inventive process, fine spherical particles are clustered together to form larger particles having high rates of absorption for aqueous fluids, particularly acceptable for use in personal care products and strong enough to minimize attrition and dusting during manufacture or use. In particular, droplets of an aqueous solution containing an α,β-ethylenically unsaturated monomer are suspended in an inert organic liquid and are polymerized and crosslinked such as to form polymer clusters. The clusters are formed by the initiation of the polymerization at the surface of the monomer droplets due to the solubility of the polymerization initiator in the inert organic liquid. In this situation, the crosslinker forms covalent chemical bonds between individual spherical particles at the exterior surfaces thereof. Once the described clusters are formed, a second crosslinking polymerization is optionally undertaken by adding a second crosslinker under polymerizing conditions to reduce coalescence of the clusters.

The water absorbent compositions of the invention may be made from a variety of polymers or copolymers. Basically, any water-soluble ethylenically unsaturated monomer or mixture thereof that crosslinks to form a substantially water insoluble gel particle in a suspension polymerization process is suitable.

Exemplary water-soluble monomers include ethylenically unsaturated amides such as acrylamide, methacrylamide, and fumaramide as well as their N-substituted derivatives;

ethylenically unsaturated carboxylic acids or esters thereof and their salts such as acrylic, methacrylic, and crotonic acids; polycarboxylic acids such as maleic, fumaric, and itaconic acid; vinyl amines such as vinyl pyridine and vinyl morpholine; and diallyl amines. Other suitable water-soluble monomers are well known to those skilled in the art as discussed by Stanley, Jr. et al. in U.S. Pat. No. 4,708,997, the relevant portions of which are incorporated herein by reference. Preferred water-soluble monomers are acrylic acid, methacrylic acid, or salts or mixtures thereof. The polymer prepared therefrom is polyacrylic acid, sodium polyacrylate or a copolymer thereof.

The water-soluble monomer is provided in an aqueous solution, such that the solution comprises from about 15 to about 40 weight percent monomer. More preferably, the aqueous solution will comprise from about 20 to about 35 weight percent monomer.

When carboxylic acid monomers are employed, the monomers are typically utilized in at least partially neutralized form. Preferably, the monomer will be neutralized to a degree from about 55 to about 90 percent, more preferably from about 60 to about 75 percent. Neutralization is typically accomplished by contacting the monomer solution with an alkali metal hydroxide, or an alkali metal carbonate or bicarbonate.

The monomer mixture typically includes one or more first crosslinkers which comprise organic compounds having two or more ethylenic groups copolymerizable with the water-soluble monomers. The first crosslinker will have a solubility in water of at least about 0.1 grams per 100 grams water, more preferably of at least about 0.15 grams per 100 grams water, as it will be desirable to retain the first crosslinker in proximity to the water-soluble monomers during suspension polymerization.

Exemplary first crosslinkers include the diacrylate or dimethacrylate of ethylene glycol, diethylene glycol, or the like, methylenebisacrylamide, triallylamine, tetraallyloxyethane, and trimethylolpropane triacrylate. For additional first crosslinkers, see U.S. Pat. No. 4,833,222 at column 5, lines 46–63, the relevant portions of which are incorporated herein by reference. First crosslinkers are typically present in the water-soluble monomer mixture in an amount effective to crosslink the resultant water-soluble polymer. Typically, the first crosslinker is used in amounts ranging from about 10 ppm to about 50,000 ppm, based on the weight of the water-soluble monomer used.

As will be described below, the first crosslinker may be provided in conjunction with one or more additional first crosslinkers and/or in conjunction with a second crosslinker. In the alternative, the first crosslinker will have both hydrophobic and hydrophilic groups, whereupon the hydrophobic groups tend to align toward the bead/organic liquid interface and the hydrophilic groups tend to align toward the interior of the bead. One such first crosslinker is trimethylolpropane triacrylate.

When trimethylolpropane triacrylate is utilized as the sole first crosslinker in an embodiment which does not employ a second crosslinker, the trimethylolpropane propane triacrylate will preferably be provided in an amount greater than about 3500 ppm, more preferably in an amount greater than about 4000 ppm, based on the weight of the water-soluble monomer. When trimethylolpropane triacrylate is utilized as the sole first crosslinker in an embodiment which does not employ a second crosslinker, the trimethylolpropane triacrylate will preferably be provided in an amount less than about 8000 ppm, based on the weight of the water-soluble monomer.

As suggested to above, it may be advantageous to employ more than one first crosslinker. For instance, rather than relying on a single crosslinker to be sufficiently hydrophilic to promote crosslinking within the interior of the polymerized monomer droplets and sufficiently hydrophobic to permit the formation of clusters, a more hydrophilic first crosslinker may be used in conjunction with a more hydrophobic first crosslinker.

The use of methylenebisacrylamide in conjunction with trimethylolpropane triacrylate as first crosslinkers leads to uniform crosslinking within the interior of the polymerized monomer droplets and to adequate clustering. The use of methylenebisacrylamide in conjunction with trimethylolpropane triacrylate as first crosslinkers further permits the use of decreased concentrations of the first crosslinker.

When methylenebisacrylamide is employed in conjunction with trimethylolpropane triacrylate as first crosslinkers, the methylenebisacrylamide will preferably be provided in an amount of at least about 1000 ppm, more preferably at least about 2000 ppm, based on the weight of the water-soluble monomer. When methylenebisacrylamide is employed in conjunction with trimethylolpropane triacrylate as first crosslinkers, the methylenebisacrylamide will preferably be provided in an amount less than about 4000 ppm, more preferably less than about 3000 ppm, based on the weight of the water-soluble monomer.

When methylenebisacrylamide is employed in conjunction with trimethylolpropane triacrylate, the trimethylolpropane triacrylate provided in the monomer solution will preferably be provided in an amount of at least about 2000 ppm, more preferably at least about 3000 ppm, and most preferably at least about 4000 ppm, based on the weight of the water-soluble monomer. When methylenebisacrylamide is employed in conjunction with trimethylolpropane triacrylate, the trimethylolpropane triacrylate provided in the monomer solution will preferably be provided in an amount less than about 8000 ppm, more preferably less than about 6000 ppm, based on the weight of the water-soluble monomer.

In another embodiment, diethylene glycol diacrylate may be used in conjunction with trimethylolpropane triacrylate as first crosslinkers. When diethylene glycol diacrylate is employed in conjunction with trimethylolpropane triacrylate as first crosslinkers, the diethylene glycol diacrylate will preferably be provided in an amount of at least about 3000 ppm, more preferably at least about 4000 ppm, based on the weight of the water-soluble monomer. When diethylene glycol diacrylate is employed in conjunction with trimethylolpropane triacrylate as first crosslinkers, the diethylene glycol diacrylate will preferably be provided in an amount less than about 12,000 ppm, more preferably less than about 10,000 ppm, based on the weight of the water-soluble monomer.

When diethylene glycol diacrylate is employed in conjunction with trimethylolpropane triacrylate as first crosslinkers, the trimethylolpropane triacrylate may be provided in the monomer solution in an amount of at least about 1000 ppm, more preferably at least about 3000 ppm, and most preferably at least about 4000 ppm based on the weight of the water-soluble monomer. When diethylene glycol diacrylate is employed in conjunction with trimethylolpropane triacrylate as first crosslinkers, the trimethylolpropane triacrylate provided in the monomer solution will preferably be provided in an amount less than about 8,000 ppm, more preferably less than about 6000 ppm, based on the weight of the water-soluble monomer.

Optionally, a second crosslinker may be provided to the inert organic phase, typically upon initiation of the polymerization. The second crosslinker serves to achieve crosslinking at the surface of the individual droplets of monomer during polymerization such that the individual polymer beads are bonded together in clusters having a substantially open pore structure that readily imbibes aqueous fluids. The second crosslinker serves to crosslink the outer surface of the polymer beads/clusters such that coalescence between clusters is minimized. The amount of second crosslinker is not critical, provided porosity of the finished clusters is not adversely affected.

When employed, the second crosslinker will typically be provided in an amount greater than about 500 ppm, more preferably greater than about 1000 ppm, and most preferably greater than about 2400 ppm, based on the weight of the water-soluble monomer. When employed, the second crosslinker will typically be provided in an amount less than about 10,000 ppm, more preferably less than about 8000 ppm, based on the weight of the water-soluble monomer. Crosslinkers suitable as a second crosslinker are, for example, trimethylolpropane triacrylate and tetraallyloxyethane.

In one system employing a first and second crosslinker, the first crosslinkers will comprise trimethylolpropane triacrylate and methylenebis-acrylamide, and the second crosslinker will comprise trimethylolpropane triacrylate. In such an embodiment, the methylenebisacrylamide will preferably be provided as a first crosslinker in the aqueous monomer solution in an amount from about 1000 to about 4000 ppm, more preferably from about 2000 to about 3000 ppm; the trimethylolpropane triacrylate will preferably be provided as a first crosslinker in the aqueous monomer solution in an amount from about 2000 to about 8000 ppm, more preferably from about 3000 to about 6000 ppm, based on the weight of the water-soluble monomer. In such an embodiment, the amount of trimethylolpropane triacrylate provided in the inert organic phase as a second crosslinker will typically be at least about 45 ppm based on the weight of the water-soluble monomer. In such an embodiment, the amount of trimethylolpropane triacrylate provided in the inert organic phase as a second crosslinker will typically be less than about 2000 ppm, preferably less than about 1450 ppm, based on the weight of the water-soluble monomer.

In another system employing a first and second crosslinker, the first crosslinker will comprise diethylene glycol diacrylate, and the second crosslinker will comprise trimethylolpropane triacrylate. In such an embodiment, the diethylene glycol diacrylate will preferably be provided in the aqueous monomer solution in an amount from about 3000 to about 12,000 ppm, more preferably from about 4000 to about 10,000 ppm, based on the weight of the water-soluble monomer. In such an embodiment, the trimethylolpropane triacrylate will preferably be provided as a second crosslinker in the inert organic liquid in an amount from about 4000 ppm to about 6000 ppm, based on the weight of water-soluble monomer.

In yet another system employing a first and second crosslinker, both the first and the second crosslinkers will comprise solely trimethylolpropane triacrylate. In such an embodiment, the trimethylolpropane will preferably be provided in the aqueous monomer solution, preferably in an amount greater than about 3500 ppm, more preferably greater than about 4000 ppm, and preferably in an amount less than about 8000 ppm, based on the weight of the water-soluble monomer. In such an embodiment, the trimethylolpropane triacrylate will preferably be provided as a second crosslinker in the inert organic liquid in an amount greater than about 5000 ppm, based on the weight of the water-soluble monomer. In such an embodiment, the trimethylolpropane triacrylate will preferably be provided as a second crosslinker in the inert organic liquid in an amount less than about 30,000 ppm, more preferably in an amount less than about 20,000 ppm, based on the weight of the water-soluble monomer.

The monomer mixture may also include components that graft polymerize onto one or more other monomer components of the mixture. One particularly suitable graft component is polyvinyl alcohol. Such graft components are typically provided in an amount from about 0 to about 10 weight percent, more typically from about 0 to about 5 weight percent, based on the weight of the water-soluble monomer.

The monomer mixture may further include a chelating agent to scavenge metal ions when a metal reactor is employed. One such chelating agent is a pentasodium salt of diethylenetriaminepentacetic acid sold under the tradename VERSENEX™ V-80 by The Dow Chemical Company (Midland, Mich.). Such a chelating agent, when employed, is typically provided in an amount from about 100 to about 2000 ppm, based on the weight of the water-soluble monomer.

In the suspension polymerization process of the invention, the monomer mixture is suspended in an inert organic liquid or oil phase which may be any organic liquid that is non-reactive with the monomers and resulting products. The inert organic liquid phase of the suspension generally comprises at least one inert hydrophobic liquid, such as a liquid hydrocarbon or substituted liquid hydrocarbon. Preferred organic liquids are the halogenated hydrocarbons such as perchloroethylene, methylene chloride and the like and liquid hydrocarbons having 4 to 15 carbon atoms per molecule, including aromatic and aliphatic hydrocarbons and mixtures thereof such as benzene, xylene, toluene, mineral oils, liquid paraffins such as kerosene, naphtha and the like. Of the foregoing organic liquids, the hydrocarbons are the more preferred with the aliphatic hydrocarbons being most preferred. A preferred commercially available aliphatic hydrocarbon is a deodorized kerosene, sold by Exxon as Isopar™ M.

The inert organic phase will typically further include a polymerization initiator system which is at least partially oil phase soluble. In particular, the reducing component of the initiator system will preferably partition such as to provide from about 10 to about 2500 ppm oxidizing agent in the inert organic phase, more preferably from about 100 to about 2500 ppm oxidizing agent in the inert organic phase, based on the weight of the water-soluble monomer. By utilizing such a system, polymerization is initiated at the interface between the monomer droplet/polymer bead surface and the inert organic phase, which promotes clustering of the polymer beads. Suitable oxidizing components include, for example, t-butyl hydroperoxide (t-BHP); 2,5-dihydroperoxy-2,5-dimethylhexane; cumene hydroperoxide, hydrogen peroxide, potassium persulfate, sodium persulfate, other alkali metal persulfates, and ammonium persulfate. The oxidizing component will preferably be present in an amount from about 20 ppm to about 600 ppm, more preferably from about 50 to about 500 ppm, based on the weight of the water-soluble monomer.

Further, sulfur dioxide may be provided as a reducing agent, typically as a 0.1 weight percent solution in nitrogen. For laboratory scale procedures preferred 0.1 weight percent sulfur dioxide solution flow rates are between about 200 and about 1000 mL/min.

Thermal initiators having sufficient oil phase solubility are also suitable, e.g., VAZO™64 azobisisobutyronitrile, available from du Pont, and benzoyl peroxide.

In the process of the invention, a suspension of very fine aqueous monomer droplets in an inert organic phase is formed. The monomer droplet size will dictate the size of the polymer beads formed. To produce clusters having the desired high surface area, the polymer beads, and thus the monomer droplets, should have a mean diameter less than about 100 microns, and more preferably less than about 80 microns. To ensure the formation of a porous cluster, the polymer beads, and thus she monomer droplets, should have a mean diameter greater than about 50 microns, more preferably greater than about 60 microns.

The inert organic oil phase includes suspending or dispersing agents that maintain the aqueous soluble monomer droplets suspended in the oil phase for the suspension polymerization. The suspending agent is chosen such that the suspension is only partially stabilized, in the sense that the clustering process of the individual polymerized beads is permitted, but general coalescence is prevented. The effective presence of the crosslinking agent and the suspending agent are balanced to achieve the clustered product of the invention that has the desired porosity without excessive fusing or coalescence.

Suitable suspending agents include surface active materials such as sucrose fatty acid esters and/or polyglycerol fatty acid esters; nonionic surface active agents having HLB values of 2–6; nonionic surface active agents having HLB values of greater than 7; polymeric materials such as the various cellulose ethers, e.g., ethyl cellulose, methyl cellulose, hydroxyethyl cellulose, hydroxypropyl cellulose, carboxyethyl cellulose or combinations thereof; hydrophobic clays such as cationic surfactant treated bentonite clays; and mixtures of fumed hydrophobic silica and copolymers of lauryl methacrylate and acrylic acid. The suspending agent may comprise a cellulose ether, provided in an amount of 0.5 weight percent, based on the weight of the monomer mixture.

A particularly preferred suspending agent is a mixture of a fumed hydrophobic silica (such as Aerosil™ R-972 manufactured by Degussa, Inc.) and a copolymer of lauryl methacrylate and acrylic acid. In a preferred copolymer, the weight ratio of lauryl methacrylate to acrylic acid in the copolymer is about 99 to 1. In a preferred embodiment, the silica will be provided in an amount of at least about 0.5 weight percent, more preferably at least about 0.7 weight percent, based on the weight of the water-soluble monomer. Preferably, the silica will be provided in an amount less than about 1.5 weight percent, more preferably less than about 1.2 weight percent, based on the weight of the water-soluble monomer. In a preferred embodiment, the lauryl methacrylate/acrylic acid copolymer will be provided in an amount of at least about 0.4 weight percent, more preferably at least about 0.8 weight percent, based on the weight of the water-soluble monomer. Preferably, the lauryl methacrylate/acrylic acid copolymer will be provided in an amount less than about 1.7 weight percent, more preferably less than about 1.3 weight percent, based on the weight of the water-soluble monomer.

The monomer droplet size is affected, in part, by the degree of the agitation of the suspension. One suitable laboratory scale mixing device is a Waring blender. It has been found that preferred mixing speeds are of at least about 400 rpm and more preferably at least about 500 rpm, when a Waring blender is employed. It has further been found that mixing speeds less than about 800 rpm, more preferably less than about 600 rpm are preferred, when a Waring blender is employed.

The reaction is carried out at any convenient temperature at which the initiator system operates efficiently. Preferably the reaction is initiated at room temperature or lower, preferably about 20° C., and proceeds adiabatically (near 50° C. to 65° C.). The reaction is initiated by bubbling the reducing agent, such as sulfur dioxide, typically diluted with nitrogen, into the reaction mixture.

After polymerization has been initiated and the temperature of the suspension mixture reaches at least about 45° C., more preferably at least about 50° C., and most preferably about 55° C., the second crosslinker is optionally added to the suspension. The second crosslinker preferably will be an ethylenically polyunsaturated monomer having substantial solubility in the inert organic continuous phase, e.g., a solubility of at least about 0.1 grams per 100 grams inert organic liquid. Preferred crosslinkers include trimethylolpropane triacrylate (TMPTA) and tetraallyl-oxyethane After the polymerization reaction is finished, the polymer product is recovered by removing the inert oil phase and drying. To achieve fast rates of absorption, the clusters of the invention will preferably be produced in a size distribution, whereupon preferably at least about 60 weight percent, more preferably at least about 70 weight percent, and most preferably at least about 80 weight percent of the clusters have a size between 30 and 170 mesh. In the alternative, the dried product may be screened to the desired size distribution.

The dried, finished product may then be treated with a wetting agent, such as VORANOL™ 2070, VORANOL™ 2100 and VORANOL™ 3100 polyols manufactured by The Dow Chemical Company TRITON™ X-100 surfactant (available from Rohm & Haas), TERGITOL™ 15-5-9, ethoxylated surfactant (available from Union Carbide), polyethylene glycols, and nonionic surfactants having an HLB value of at least 7. The wetting agent helps overcome the adverse effect of any residual dispersing agent, such as hydrophobic inert inorganic silica material, remaining on the finished product.

The desired amount of wetting agent may be determined empirically, bearing in mind that in industrial practice it is desirable to minimize the amount of additive for economic reasons. Typically, however, the wetting agent will be provided in an amount from about 0.1 to about 2.5 weight prevent, preferably from about 0.3 to about 1.5 weight percent, and more preferably from about 0.5 to about 1 weight percent, based upon the weight of the polymer clusters.

The wetting agent may be applied as a dispersion in a solvent, such as methanol, which solvent is subsequently removed. In the alternative, the wetting agent may be applied neat to the polymer clusters with mixing, as described in PCT application publication number WO 93/24153 corresponding to U.S. patent application Ser. No. 891,376, the relevant portions of which are incorporated herein by reference.

FIG. 1 provides a photomicrograph of polymer clusters of the invention, prepared in accordance with Example 6 below, at a magnification of 50 times. FIG. 1 demonstrates the unique and exceptionally high surface area of polymer particle clusters available for absorbing aqueous fluids, due in large part, to the high porosity of the clusters.

In characterizing the finished water-absorbent polymers of the invention, particle size distribution of the clusters, vortex rate, absorption under load (AUL) are measured AUL measures the ability of a polymer to swell against a pressure of 0.3 psi (2 kPa), which pressure simulates the pressures that the polymer must swell against in a diaper. In the test procedure, 0.160 gram of the polymer of interest is placed in a cylinder including a Whatman GF-A filter paper resting on a 100 mesh (149 micrometers) screen. A loose fitting cover is placed on top of the polymer and a 100 gram weight is placed on top of the cover. The polymer is exposed to 0.9 percent NaCl solution by means of an apparatus that maintains the level of the saline reservoir such that there is no hydrostatic head pressure. The amount of liquid absorption after 5 minutes and 60 minutes is measured as 5 minute AUL and 60 minute AUL, respectively.

The gel blocking characteristics of a polymer can be determined by comparing the 5minute AUL with its 60 minute AUL value. Materials that gel block absorb liquids very slowly under pressure, because the gel particles are easily deformed forming a nonporous gel network that has poor fluid transport properties. This results in a low value for the 5 minute AUL relative to the 60 minute AUL value.

Vortex rate is measured by weighing 50 grams of a 0.9 percent aqueous sodium chloride solution into a 100 mL beaker. The beaker is placed on a magnetic stirrer such that there is a substantial vortex. To the side of the vortex, 2 grams of the sample to be tested is added. The time is started when all the sample has been added; the time is stopped when the vortex disappears (the vortex rate being the latter time). Samples that do not gel block form firm gels that maintain an open structure giving good fluid transport. For these materials the 5 minute and 60 minute AUL's are very close together.

Preferred cluster products of the invention will be characterized by 5 minute AUL that are very close to their 60 minute AUL's e.g. a 5 minute AUL which is at least about 80 percent of the 60minute AUL for the same sample.

The polymers of the invention may be utilized as a principal absorbing component of a personal care product. A typical personal care product is a disposable diaper wherein the polymer of the invention is contained in a composite structure generally comprising an exterior impervious sheet and a porous interior sheet with the polymer of the invention, optionally mixed with cellulose fibers, sandwiched between said sheets.

The following examples illustrate the products and process of the invention and are not intended to limit the invention only to their scope.

EXAMPLES 1–29

An aqueous monomer mixture is formed by adding to 172.8 grams of water: 116 grams of acrylic acid; 110 grams of a 50 percent aqueous solution of sodium hydroxide; 0.23 grams methylenebisacrylamide; 4.6 grams of a 10 percent aqueous solution of VERSENEX 80 chelating agent (a pentasodium salt of diethylenetriamine pentacetic acid for scavenging metal compounds) supplied by The Dow Chemical Company; and, as a first portion of a partially continuous organic phase soluble crosslinker, the amount of trimethylolpropane triacrylate (TMPTA) indicated in Table I as "first crosslinker".

A continuous medium organic phase is formulated at low speed in a Waring blender/mixer, including 400 grams of ISOPAR™ M, a hydrocarbon supplied by Exxon Chemicla Co; and a suspending agent that is a mixture of 0.3 grams of AEROSIL™ R-972 (a hydrophobic silica supplied by Degussa, Inc; and 0.48 grams of a copolymer of 1 percent by weight acrylic acid and 99 percent by weight laurylmethacrytate.

To 200 g of the aqueous monomer solution, 0.5 mL of a 6.1 percent aqueous solution of sodium persulfate is added. The organic phase is mixed for 10 seconds at low speed in the Waring blender. The speed of the blender is increased to 800 rpm and the 200 g of the aqueous solution is added and stirred for 30 seconds. The resulting suspension is transferred to a reactor, where it is purged for 30 minutes with nitrogen. To the purged mixture, 1 mL of an 8.9 percent aqueous solution of t-butyl hydroperoxide is added. The suspension is purged an additional 10 minutes.

The polyacrylate polymerization is initiated by bubbling sulfur dioxide diluted in nitrogen into the reaction mixture. The agitation rate in the reactor is as indicated in Table I.

When the mixture temperature reaches 50° C., (unless otherwise indicated in Table I), the indicated amount of trimethylolpropane triacrylate as a "second crosslinker" is added. The reaction proceeds exothermically and is maintained at a temperature of 65° C. for one hour.

The ISOPAR hydrocarbon organic phase is then removed by filtration and the polymer product dried. The dry polymer is slurried in a mixture of 0.03 grams of VORANOL™ 2070 polyol, available from The Dow Chemical Company (Midland, Mich.), in methanol to provide 1 weight percent polyol based on the weight of the polymer material. The methanol is removed by vacuum stripping at 80° C.

The aqueous absorbent polymer material of the invention which comprises clusters of a plurality of individual particles of absorbent polymer, is analyzed for particle size distribution, vortex rate, 5 minute 0.3 psi AUL and 60 minute 0.3 psi AUL. These data appear in Table 1 below.

TABLE I

| Example | Amount of first crosslinker (g) | Amount of second crosslinker (g)[1] | Agitation rate (rpm) | Vortex rate (sec) | AUL (g/g) 5 min | AUL (g/g) 60 min | Centrifuge Capacity (g/g) |
| --- | --- | --- | --- | --- | --- | --- | --- |
| 1 | 0.345 | 0.55 | 400 | 41 | 16.9 | 20.0 | 19.1 |
| 2 | 0.345 | 0.55 | 600 | 2.6 | 23.0 | 24.2 | 22.9 |
| 3 | 0.345 | 0.55 | 800 | 15.7 | 22.6 | 23.6 | 20.4 |
| 4 | 0.345 | 0.55 | 800 | 5.0 | 24.3 | 25.1 | 22.6 |
| 5 | 0.46 | 0.55 | 400 | 3.9 | 25.1 | 26.0 | 24.0 |
| 6 | 0.46 | 0.55 | 600 | 6.0 | 24.8 | 25.4 | 23.2 |
| 7 | 0.46 | 0.55 | 600 | 15.4 | 20.7 | 22.6 | 19.3 |
| 8 | 0.46 | 0.55 | 600 | 3.1 | 24.9 | 25.8 | 24.3 |

TABLE I-continued

| Example | Amount of first crosslinker (g) | Amount of second crosslinker (g)[1] | Agitation rate (rpm) | Vortex rate (sec) | AUL (g/g) 5 min | AUL (g/g) 60 min | Centrifuge Capacity (g/g) |
|---|---|---|---|---|---|---|---|
| 9 | 0.46 | 0.55 | 600 | 2.9 | 24.8 | 26.4 | 24.3 |
| 10 | 0.46 | 0.55 (40° C.) | 600 | 2.3 | 23.7 | 24.6 | 22.5 |
| 11 | 0.46 | 0.55 (45° C.) | 600 | 5.3 | 23.1 | 24.4 | 22.4 |
| 12 | 0.46 | 0.55 (45° C.) | 600 | 5.4 | 23.3 | 24.7 | 22.8 |
| 13 | 0.46 | 0.55 (54.5° C.) | 600 | 2.3 | 23.7 | 24.6 | 22.5 |
| 14 | 0.46 | 0.55 (54.5° C.) | 600 | 5.5 | 23.1 | 24.5 | 22.2 |
| 15 | 0.46 | 0.55 (54.5° C.) | 600 | 8.6 | 25.1 | 25.6 | 24.2 |
| 16 | 0.46 | 0.55 (54.5° C.) | 600 | 2.8 | 15.0 | 15.3 | 13.8 |
| 17 | 0.46 | 0.55 (54.5° C.) | 600 | 8.9 | 25.1 | 26.9 | 24.8 |
| 18 | 0.46 | 0.55 (54.5° C.) | 600 | 10.3 | 23.7 | 24.0 | 21.9 |
| 19 | 0.46 | 0.55 (54.5° C.) | 600 | 9.4 | 24.8 | 26.5 | 23.3 |
| 20 | 0.46 | 0 | 600 | 9.8 | 21.0 | 22.6 | 20.8 |
| 21 | 0.46 | 0.55 | 800 | 5.3 | 25.5 | 26.2 | 24.0 |
| 22 | 0.46 | 0.55 | 800 | 4.5 | 24.2 | 25.4 | 23.0 |
| 23 | 0.46 | 0.55 | 800 | 5.6 | 23.1 | 25.1 | 24.8 |
| 24 | 0.46 | 1.65 | 400 | 39 | 6.0 | 19.7 | 22.4 |
| 25 | 0.46 | 1.65 | 600 | 14.5 | 21.4 | 23.3 | 19.8 |
| 26 | 0.46 | 1.65 | 800 | 14.9 | 21.0 | 23.0 | 21.3 |
| 27 | 0.575 | 0.55 | 400 | 4.0 | 23.9 | 25.9 | 24.5 |
| 28 | 0.575 | 0.55 | 600 | 2.7 | 23.4 | 24.8 | 24.0 |
| 29 | 0.575 | 0.55 | 800 | 2.2 | 24.6 | 25.9 | 24.4 |

[1]Second crosslinker was added when reaction mixture was at 50° C., unless otherwise indicated

EXAMPLES 30–43

The process of Examples 1–29 is repeated, except that 97 grams of the 50 percent aqueous solution of sodium hydroxide, rather than 110 grams is used and except that no methylenebisacrylamide is used. Further modifications are indicated in Table II, which provides the amount of trimethylolpropane triacrylate utilized as a first and second crosslinker and the amount of suspending aids used. The second crosslinker is added when the reaction mixture is at 50° C. The agitation rate during reaction is 500 rpm, except for Examples 31 and 38, in which it is 600 rpm.

Examples 30–43 indicate that systems which employ solely a predominantly oil phase soluble crosslinking agent are feasible.

Examples 44–69

The process of Examples 1–29 is repeated, except that in Examples 44–60 the amount of Aerosil R972 employed is 0.6 grams and the amount of the polylaurylmethacrylate/acrylic acid copolymer employed is 0.96 grams. In Examples 44–69, the amounts of trimethylolpropane triacrylate used as the first crosslinker and as the second crosslinker are 0.46 and 0.55 grams, respectively, the second crosslinker being added when the reaction mixture is at 50° C. The ratio of the weight of the inert organic phase to the weight of the aqueous monomer solution and the agitation rate during reaction are as indicated in Table III.

TABLE II

| Example | Amount of suspending aids Present wt % based on AA AEROSIL | Amount of suspending aids Present wt % based on AA LMA/AA | Amt of TMPTA added | | Vortex rate (sec) | AUL (g/g) 5 min | AUL (g/g) 60 min | Centrifuge Capacity (g/g) |
|---|---|---|---|---|---|---|---|---|
| 30 | 0.776 | 0.414 | 0.29 | 0.29 | 2.5 | — | — | 25 |
| 31 | 0.776 | 0.414 | 0.29 | 0.29 | 4.1 | 4.4 | 7.4 | 26.5 |
| 32 | 1.034 | 0.828 | 0.35 | 0 | 8.4 | 4.5 | 8.3 | 27.8 |
| 33 | 1.034 | 0.414 | 0.35 | 0.58 | 3.1 | 18.5 | 19.6 | 19.5 |
| 34 | 1.034 | 0.414 | 0.35 | 1.2 | 3.3 | 19.9 | 20.4 | 17.7 |
| 35 | 1.034 | 0.414 | 0.35 | 1.7 | 1.5 | 10.6 | 17.6 | 25 |
| 36 | 1.034 | 0.414 | 0.35 | 0.29 | 1.8 | 18.5 | 22.7 | 22.6 |
| 37 | 1.034 | 0.414 | 0.35 | 0.35 | 2.6 | — | — | 24 |
| 38 | 1.034 | 0.414 | 0.35 | 0.35 | 9.1 | — | — | 22.2 |
| 39 | 0.517 | 0.414 | 0.35 | 0.35 | 4.0 | 19.0 | 20.1 | 18.2 |
| 40 | 0.776 | 0.414 | 0.35 | 0.35 | 4.7 | 5.2 | 8.5 | 23.3 |
| 41* | 1.034 | 0.828 | 0.46 | 0 | 3.1 | — | — | — |
| 42 | 1.034 | 0.414 | 0.46 | 0 | 4.1 | — | — | — |
| 43 | 0.507 | 0.828 | 0.92 | 0 | 11.3 | — | — | — |

*Rather than a 2:1 ratio between the inert organic phase and the aqueous phase, a 1.5:1 ratio is employed.

TABLE III

| Example | Oil: Aqueous ratio | Agitation rate during reaction (rpm) | Vortex rate (sec) | 0.3 psi AUL (g/g) 5 min | 0.3 psi AUL (g/g) 60 min | Centrifuge Capacity (g/g) |
|---|---|---|---|---|---|---|
| 44 | 2:1 | 600 | 6.0 | 24.8 | 25.4 | 23.2 |
| 45 | 2:1 | 600 | 15.4 | 20.7 | 22.6 | 19.3 |
| 46 | 2:1 | 600 | 3.1 | 24.9 | 25.8 | 24.3 |
| 47 | 2:1 | 600 | 2.9 | 24.8 | 26.4 | 24.3 |
| 48 | 1.75:1 | 600 | 4.1 | 24.9 | 26.0 | 23.4 |
| 49 | 1.5:1 | 600 | 4.0 | 26 | 26.3 | 23.3 |
| 50 | 1.25:1 | 600 | 4.7 | 24.6 | 26.5 | 23.5 |
| 51 | 1.0:1 | 600 | 27.1 | 19.4 | 20.8 | 20.0 |
| 52 | 1.75:1 | 500 | 5.2 | 24.6 | 24.9 | 21.8 |
| 53 | 1.5:1 | 500 | 7.0 | 24.2 | 24.4 | 24.1 |
| 54 | 1.25:1 | 500 | — | — | — | — |
| 55 | 1.0:1 | 500 | — | — | — | — |
| 56 | 2:1 | 400 | 3.9 | 25.1 | 26.0 | 24.0 |
| 57 | 1.75:1 | 400 | — | — | — | — |
| 58 | 1.5:1 | 400 | — | — | — | — |
| 59 | 1.25:1 | 400 | — | — | — | — |
| 60 | 1.0:1 | 400 | — | — | — | — |
| 61 | 2:1 | 600 | 14.9 | 22.7 | 23.3 | 20.7 |
| 62 | 1.5:1 | 600 | 38.9 | 20.2 | 21.3 | 19.2 |
| 63 | 1:1 | 600 | 11.2 | 21.0 | 24.2 | 21.2 |
| 64 | 2:1 | 500 | — | — | — | — |
| 65 | 1.5:1 | 500 | 7.3 | 24.6 | 25.0 | 21.8 |
| 66 | 1:1 | 500 | 8.2 | 23.9 | 24.5 | 21.2 |
| 67 | 2:1 | 400 | 11.4 | 22.9 | 23.7 | 21.3 |
| 68 | 1.5:1 | 400 | 9.6 | 23.5 | 24.3 | 22.0 |
| 69 | 1:1 | 400 | — | — | — | — |

EXAMPLES 70–80

The process of Examples 1–29 is repeated, except that no methylenebisacrylamide is used, with diethyleneglycoldiacrylate being provided as a first crosslinker in the amount indicated in Table IV. In Examples 70–76, trimethylolpropane triacrylate is provided as an additional first crosslinker; in Examples 77–80, trimethylolpropane triacrylate is provided as a second crosslinker when the reaction is at a temperature of 50° C. The agitation rate during reaction and the amounts of trimethylolpropane triacrylate employed are as set forth in Table IV.

TABLE IV

| Example | Amt of DEGDA (ppm based on acrylic acid) | Amt of TMPTA (ppm based on acrylic acid) | Agitation rate (rpm) | Vortex rate (sec) | 0.3 psi AUL (g/g) 5 min | 0.3 psi AUL (g/g) 60 min | Centrifuge Capacity (g/g) |
|---|---|---|---|---|---|---|---|
| 70 | 4,000 | 4,000 | 500 | 3.2 | 18.9 | 23.9 | 25.2 |
| 71 | 4,000 | 8,000 | 500 | 2.1 | 21.7 | 25.5 | 25.2 |
| 72 | 6,000 | 6,000 | 500 | 4.0 | 24.1 | 25.1 | 25.1 |
| 73 | 8,000 | 4,000 | 500 | 5.7 | 24.1 | 24.5 | 22.4 |
| 74 | 8,000 | 6,000 | 500 | 4.3 | 27.0 | 27.3 | 26 |
| 75 | 10,000 | 4,000 | 500 | 4.1 | 24.8 | 26.1 | 25.3 |
| 76 | 10,000 | 6,000 | 500 | 5.2 | 21.1 | 22 | 21.7 |
| 77 | 3,000 | 10,000 | 400 | 9.6 | 14.9 | 15.1 | 15 |
| 78 | 4,000 | 10,000 | 500 | 4.8 | 18.4 | 19.8 | 19.1 |
| 79 | 6,000 | 5,000 | 500 | 14 | 8.9 | 15.4 | 17.3 |
| 80 | 6,000 | 10,000 | 500 | 5.0 | 21.1 | 21.7 | 20.7 |

What is claimed is:

1. A process for preparing a polymer material, consisting essentially of:
   (a) suspending an aqueous monomer mixture comprising a water soluble ethylenically unsaturated monomer in an inert organic liquid to form a suspension having a discontinuous phase of monomer droplets, said monomer mixture including a first polyethylenically unsaturated crosslinker having a solubility in water of at least about 0.1 grams crosslinker to 100 grams water, said suspension further containing a polymerization initiator which will partition such as to provide at least about 10 ppm polymerization initiator in said inert organic liquid, said suspension further containing a suspending agent to partially stabilize said suspension;
   (b) initiating the polymerization of said monomer and said first crosslinker such that a crosslinking polymerization occurs at the interface between the monomer droplets and organic liquid, wherein individual particles of polymer are bonded together to form clusters and wherein during said polymerization, a second polyethylenically unsaturated crosslinker having a solubility in the organic liquid continuous phase greater than about 0.1 grams per 100 grams organic liquid continuous phase is added; and c) further polymerizing said clusters and second crosslinker such that further polymerization occurs at the cluster/organic phase interface.

2. The process of claim 1 wherein said ethylenically unsaturated monomer is an amide, carboxylic acid or its esters, vinyl amine, or their salts or mixture thereof.

3. The process of claim 1 wherein said polymer is crosslinked polyacrylic acid, crosslinked sodium polyacrylate or a crosslinked copolymer of acrylic acid and sodium acrylate.

4. The process of claim 1 wherein said monomer mixture also includes a component which graft polymerizes onto one or more other monomer components of the mixture.

5. The process of claim 4, wherein said component is polyvinyl alcohol.

6. The process of claim 5, wherein said clusters are greater than 75 micrometers in diameter.

7. The process of claim 6, wherein 2 grams of said clusters have a vortex rate of absorption of 50 grams of a 0.9 percent aqueous sodium chloride solution of less than 60 seconds.

8. The process of claim 1 further comprising:

(e) applying a wetting agent to said clusters.

9. The process of claim 8, wherein said wetting agent is a polyol.

10. The process of claim 1 wherein said suspending of said monomer mixture to form fine monomer droplets comprises agitating said monomer mixture at high shear rates.

11. The process of claim 1 wherein said suspending agent comprises a cellulose ether, provided in an amount of 0.5 weight percent, based on the weight of said monomer mixture.

12. The process of claim 1 wherein said suspending agent comprises a nonionic surface active composition having an HLB value greater than 7.

13. The process of claim 1 wherein said suspending agent comprises a mixture of hydrophobic silica and a copolymer of lauryl methacrylate and acrylic acid.

14. The process of claim 1 wherein said first crosslinker is trimethylol propane triacrylate (TMPTA), the diacrylate or dimethacrylate of ethylene glycol, the diacrylate or dimethacrylate of diethylene glycol, methylenebisacrylamide, triallyamine, tetraallyloxyethane, or combinations thereof.

15. The process of claim 14, wherein said first crosslinker comprises TMPTA in an amount of at least about 2000 ppm to less than 8000 ppm, based on the weight of said monomer.

16. The process of claim 14, wherein said second crosslinker is trimethylolpropane triacrylate (TMPTA) or tetraallyloxyethane.

17. The process of claim 16, wherein the second crosslinker comprises TMPTA in an amount from about 5000 ppm to about 20,000 ppm, based on the weight of said monomer.

18. The process of claim 1 wherein said polymerization initiator is t-butyl hydroperoxide, cumene hydroperoxide, or 2,5-dihydroperoxy-2,5-dimethylhexane.

19. The process of claim 18, wherein said initiating of step (b) is accomplished by introducing sulfur dioxide into said suspension.

* * * * *